(12) United States Patent
Rawat et al.

(10) Patent No.: US 10,444,210 B2
(45) Date of Patent: Oct. 15, 2019

(54) SYSTEM AND METHOD FOR REAL-TIME CARBON EMISSIONS CALCULATION FOR ELECTRICAL DEVICES

(71) Applicant: Cooper Technologies Company, Houston, TX (US)

(72) Inventors: Payal Rawat, Magarpatta (IN); Shravana Kumar Musunuri, Viman Nagar (IN); Rahul Panday, Maharashtra (IN); Sneha Shirish Khole, Pune (IN); Ragini Jain, Pune (IN); Rohit Joshi, Uttarakhand (IN)

(73) Assignee: Baton Intelligent Power Limited, Dublin (IE)

( * ) Notice: Subject to any disclaimer, the term of this patent is extended or adjusted under 35 U.S.C. 154(b) by 383 days.

(21) Appl. No.: 15/223,256

(22) Filed: Jul. 29, 2016

(65) Prior Publication Data
US 2018/0031533 A1 Feb. 1, 2018

(51) Int. Cl.
*G01N 33/00* (2006.01)
*G06Q 50/06* (2012.01)

(52) U.S. Cl.
CPC ......... *G01N 33/0036* (2013.01); *G06Q 50/06* (2013.01); *Y02E 40/76* (2013.01);
(Continued)

(58) Field of Classification Search
CPC ... G01N 33/0036; G01N 33/004; G06Q 50/06
See application file for complete search history.

(56) References Cited

U.S. PATENT DOCUMENTS

| 8,818,758 B1 | 8/2014 | Singh et al. |
| 10,014,691 B2 * | 7/2018 | Haynes ..................... H02J 3/14 |

(Continued)

FOREIGN PATENT DOCUMENTS

| CN | 202550230 U | 11/2012 |
| CN | 203366310 U | 12/2013 |
| WO | 2015012778 A2 | 1/2015 |

OTHER PUBLICATIONS

Samad et al., "Automated Demand Response for Smart Buildings and Microcrids: The state of the practice and research challenges", IEEE 104(4) Apr. 2016.*

*Primary Examiner* — Mohamed Charioui
*Assistant Examiner* — Catherine T. Rastovski
(74) *Attorney, Agent, or Firm* — Ziolkowski Patent Solutions Group, SC

(57) ABSTRACT

A system and method for calculating real-time carbon emissions at a distribution substation level and at an individual device level is disclosed. A substation controller is provided at the utility substation that is in operable communication with one or more devices via a demand response protocol, the demand response protocol including demand response signals transferrable from the substation controller to the one or more devices and demand response signals transferrable from the one or more devices to the substation controller. A carbon emissions calculator module is embedded in the substation controller and/or the devices that is programmed to identify or receive power consumption data from respective devices and calculate carbon emissions for the respective devices based on the power consumption data. Carbon emissions data may be provided to the substation controller to provide for a determination and output of the calculated carbon emissions for each of the one more devices.

17 Claims, 5 Drawing Sheets

(52) U.S. Cl.
CPC ............ *Y02P 90/84* (2015.11); *Y02P 90/845* (2015.11); *Y04S 10/545* (2013.01)

(56) References Cited

U.S. PATENT DOCUMENTS

| | | |
|---|---|---|
| 2009/0125436 A1 | 5/2009 | Palanchian et al. |
| 2010/0077020 A1 | 3/2010 | Paloheimo et al. |
| 2010/0249955 A1* | 9/2010 | Sitton .................... G05B 15/02 700/33 |
| 2012/0204044 A1* | 8/2012 | Lee .......................... H02J 3/14 713/320 |
| 2014/0207415 A1 | 7/2014 | Bhutani et al. |
| 2014/0222665 A1* | 8/2014 | Kamel ............... G01R 21/1333 705/39 |
| 2016/0362800 A1* | 12/2016 | Ren .......................... C25B 1/18 |

\* cited by examiner

SYSTEM AND METHOD FOR REAL-TIME CARBON EMISSIONS CALCULATION FOR ELECTRICAL DEVICES

BACKGROUND OF THE INVENTION

Embodiments of the present invention relate generally to the monitoring of carbon emissions and, more particularly, to a system and method for calculating real-time carbon emissions at a distribution substation level and at an individual device level.

According to the U.S. Department of Energy, Americans emit over seven billion metric tons of greenhouse gases into the atmosphere each year. Greenhouse gases include water vapor, carbon dioxide, methane, nitrous oxide, chlorofluorocarbons, hydrochlorofluorocarbons, ozone, hydrofluorocarbons, perfluorocarbons and sulfur hexafluoride. Most of the electricity Americans currently receive is sourced from power plants that use fossil fuels to generate electricity.

Consumers of energy, whether individuals, corporations, or other entities, have become increasingly concerned with energy consumption in its conventional form. This is manifested in the global energy crisis, the effect fossil fuels are having on the environment, and other social concerns. Increasingly, the world community is seeking alternatives to reduce the impact of fossil fuels which include coal, oil, or natural gas. These alternatives include reducing overall consumption, increasing energy efficiency, and exploiting natural and renewable resources.

It is the burning of fossil fuels that is largely responsible for greenhouse gas emissions which have now been linked to climate change. Climate change includes human activities that alter the atmospheric conditions (e.g., temperature, precipitation, wind, etc.) or affect the land surface of the earth (e.g., deforestation, reforestation, urbanization, desertification, etc.). Climate change caused by excessive fossil fuel use has also been associated with an increase in severe weather events, including higher temperatures, melting icecaps, flooding and drought.

Climate change and environmental protection awareness have created a need for both a reduction in energy consumption and carbon emission calculation tools for tracking the carbon footprint of people and industries, with norms and efficiency targets being devised by governments and environmental protection agencies to reduce energy consumption and carbon footprints.

One mechanism to address the desire to reduce energy consumption is the implementation of demand response ("DR") systems—which is a technology-enabled economic rationing system for electric power supply. In DR systems, voluntary rationing is accomplished by price incentives—offering lower net unit pricing in exchange for reduced power consumption in peak periods. DR systems and their programs are thus designed to decrease electricity consumption or shift it from on-peak to off-peak periods depending on consumers' preferences and lifestyles—thereby attempting to reduce the amount of power that needs to be generated by a power generation plant during peak periods and thereby reduce the accompanying burning of fossil fuels.

In calculating carbon emission for tracking the carbon footprint of people and industries, existing carbon emission calculators are deployed only at a power generation plant level. However, the useage of such carbon emission calculators at the power generation plant level provides only a rough estimate of carbon emissions, with it being recognized that there is no mechanism to calculate the exact carbon footprint at the distribution level or at the electrical device level (i.e., for each electrical device connected to the utility). As one example, there is no existing way to accurately estimate carbon reduction emissions resulting from generation of solar power at the load/distribution side. As another example, there is no existing way (except for estimation methods presently in use) of determining the reduction of carbon emissions associated with DR events, as the utility/generation facility is not aware of the true responsiveness of the loads associated with the DR control.

The inability of the utility to determine the reduction of carbon emissions in real time and, in particular, with the DR events prevents the utility from being able to gauge exactly which geographical areas are employing/implementing "green" technologies or factors, or to-say "green savvy" areas, and which geographical areas are not. Accordingly, there is no way to identify the potential areas within a utility coverage region that are emitting a maximum level of carbon gasses and recommending solutions to reduce such emissions.

Therefore, it would be desirable to provide a system and method capable of automatically determining the carbon emissions at each of a device and substation level. It would further be desirable to allow for the calculated values to be aggregated at the utility level to geographically visualize the high-emission areas and green geographical areas. With solar power data at distribution level also being considered, an accurate manner of assessing carbon emissions in a particular industry or locality can be provided.

BRIEF DESCRIPTION

In accordance with one aspect of the present invention, a system to calculate the carbon emissions of one or more devices operably connected to a utility substation to receive power therefrom is provided. The system includes a substation controller provided at the utility substation and in operable communication with the one or more devices via a demand response protocol, the demand response protocol including demand response signals transferrable from the substation controller to the one or more devices and demand response signals transferrable from the one or more devices to the substation controller. The system also includes a carbon emissions calculator module embedded in or operably connected to the substation controller, the carbon emissions calculator programmed to receive at least one of power consumption data and load information values from each of the one more devices via the demand response protocol, calculate carbon emissions for each of the one more devices based on the at least one of power consumption data and load information values, and generate an output indicating the calculated carbon emissions for each of the one more devices.

In accordance with another aspect of the present invention, a system to calculate the carbon emissions of a power consuming device operably connected to a utility substation to receive power therefrom is provided. The system includes a power consuming or power monitoring device and a device controller configured to provide load control and power consumption modification for the device, the device controller in operable communication with the utility substation via a demand response protocol that comprises demand response signals transferrable from the utility substation to the device controller and demand response signals transferrable from device controller to the utility substation. The system also includes a carbon emissions calculator module embedded in or operably connected to the device controller, the carbon emissions calculator programmed to monitor a real-time power consumption of the device, calculate carbon emissions for the device based on the monitored power consumption, and generate an output signal comprising the calculated carbon emissions for the device, the output signal being transmittable to the utility substation via the demand response protocol.

In accordance with yet another aspect of the present invention, a method for calculating the carbon emissions of one or more devices operably connected to a utility substation includes a step of providing a demand response system configured to implement a demand response protocol for interactions between a substation controller and the one or more devices, the demand response protocol including demand response signals transferrable from the substation controller to the one or more devices and demand response signals transferrable from the one or more devices to the substation controller to provide load control and power consumption modification for the one or more devices. The method also includes the steps of determining a power consumption of each of the one more devices resulting from an operation thereof and calculating, via a carbon emissions calculator module embedded in one of the substation controller or a respective device of the one or more devices, carbon emissions for each of the one more devices based on the power consumption.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

Embodiments of the invention are directed to a system and method for calculating the real-time carbon emissions at an electrical distribution substation and electrical device level. A carbon emissions calculator may be embedded in the electrical software residing in a distribution substation or may be embedded in an individual product or device, with load information and demand response events of the devices being analyzed to calculate the real-time carbon emissions and emissions reductions achieved.

Figure 1:
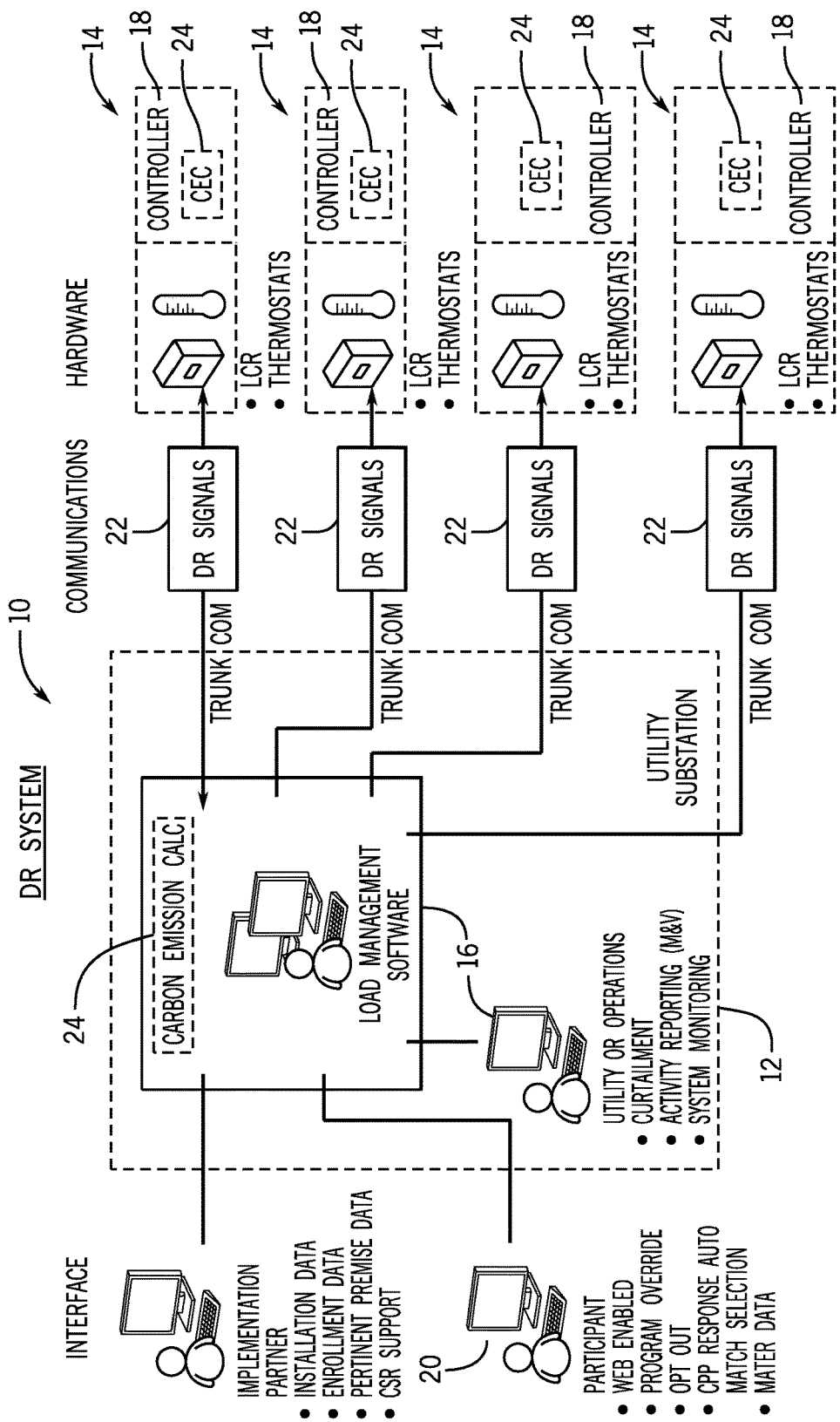
FIG. 1 is a schematic diagram of a demand response (DR) system that includes an electrical distribution substation in communication with a plurality of connected devices, according to an embodiment of the invention.

Referring to FIG. 1, an implementation of demand response (DR) logic within a DR system 10 is illustrated, in and with which embodiments of the invention might be implemented. As shown in FIG. 1, the DR system 10 is generally comprised of an electrical distribution substation 12 that manages the distribution of power to numerous DR resources 14—in the form of loads and devices such as, for example, load control switches, power meters (e.g., LCR meters), and thermostats—that receive power from the substation 12. The DR system 10 is a system that may be used by utilities and independent system operators (ISO's) to manage the operation of DR programs. A focus of the DR system 10 may be on the operational aspects of managing the selection, signaling, and monitoring of the DR resources 14 (i.e., loads and devices) that are participating in DR programs. The DR system 10 may be specifically designed to manage the operations of automated DR programs according to various logic components of the DR system 10.

For implementing a DR program in the DR system 10, the system and associated software may be implemented and operated with one or more computers, controllers, or processors and associated connections—with such computers/controllers/processors being provided at the substation, indicated at 16, embedded in the DR resources 14, indicated at 18, and being programmed to include DR logic that implements a DR program in the system 10. In one embodiment, a computer 16 is provided at the substation to implement the DR logic thereat, with the computer incorporating one or more inputs, a processor, a user interface with a keyboard and display, a memory, external connections such as an internet, one or more outputs, and so forth (not shown). The customer/consumer may also interact with the controller or processor 18 embedded in the DR resource 14 (such as via a separate web or wi-fi connected computer or mobile device 20) to control various settings or operating parameters thereof (as set in controller/processor 18) as part of the DR program, with the controller/processor 18 of the DR resource 14 being programmable via inputs received therefrom via the substation computer 14 and/or customer device 20. There may be various types of interactions that might occur between the utility and a DR resource 14 as part of the DR program, with such interactions being provided as DR signals 22 going from the utility substation 12 to the DR resource 14 and/or as DR signals 22 going from the DR resource 14 to the utility substation 12.

In operating DR system 10, it is recognized that, at the highest level, there may virtually always be some sort of grid condition, be it economic or grid reliability in nature, which triggers a so-called DR event that requires some sort of interaction between the utility substation 12 and its customers and associated DR resources 14. This interaction may eventually trigger some sort of load control taking place at a customer's facility/residence—which is termed as a "DR event." The interaction between the utility substation 12 and the DR device 14 of the customer may be mediated by the DR signals 22. It is the information contained within the DR signals 22 that may dictate where much of the decision making takes place in how the initial grid condition that triggered the DR event results in the eventual load control.

With regard to the generation of DR signals 22, the types of DR interactions and signals that may be used between the utility substation 12 and the DR resources 14 includes information/instructions that encompass a supply state, DR resource instructions, and load controller commands. A supply state may refer to information about conditions concerning the supply of electricity that may affect the DR resource's load profile. The conditions may incorporate prices of electricity, sources of generation (e.g., solar versus coal), carbon content, reliability of supply or grid conditions, and other conditions. DR resource instructions may refer to information that specifies what the load profile of a DR resource 14 should be as a result of receiving a DR signal 22. Examples of this information may incorporate specific consumption levels (which can be either up or down), dispatch instructions, and load profile specifications. Load controller commands may refer to specific load control commands sent to the controller 18 of a DR device 14 that specifies the state that the device/load should be in. Examples may incorporate existing DR programs such as AC cycling in which air conditioners within residences are turned on and off, with this information being used for direct load control.

With regard to supply state information, the information may be such that it does not necessarily include any specific instructions for how the load profile of the DR resource 14 should change. Virtually all decisions as to what the desired load profile should be in response to the information within a DR signal 22 may be within the DR resource 14. A very typical example of this type of DR signal 22 may be real-time or dynamic electricity prices that may be sent to a DR resource 14. With regard to DR resource instructions, this type of information may be more specific than information of the supply state, in that it indicates what the load profile of DR resource 14 should be. The information does not necessarily indicate how individual loads of the DR resource 14 should be controlled and thus the intelligence for determining how to control individual loads may be virtually all within DR resource 14. The information may be about load shifting or shedding, and the certainty or predictability of a load shape change.

According to an exemplary embodiment, the electrical distribution substation 12 may be operated via a Yukon® Advanced Energy Services Platform from Eaton Corporation (i.e., "Yukon"), with the Yukon® program providing a two-way wireless mesh network the utility substation 12 and connected DR devices 14. The Yukon® program provides an intuitive, flexible interface that allows operators to easily initiate targeted DR events as wide as full system or as small as individual distribution feeders and enables control options for the utility and participating customers that range from directly controlling DR devices 14 configured for a level of participation either by the utility or chosen by the consumer, to notifying a consumer or triggering a secondary on site management system to perform the load reduction. The Yukon® program also provides simple access to time critical information such as active events and historical event history to support the enhanced grid management techniques. In operation, the Yukon program may thus manage DR interactions and signals that may be used between the utility 12 and the DR resources 14, including supply state, DR resource instructions, and load controller commands.

According to embodiments of the invention, the DR system 10 not only provides for implementation of a DR program for initiating targeted DR events at a full system or individual distribution feeder or device level, but additionally provides for calculating the real-time carbon emissions at a distribution substation level and/or at an individual device level. A carbon emissions calculator, identified at 24, may be embedded in the electrical software of the computer 16 residing in the distribution substation 12 or may be embedded in the controller/processor 18 of an individual DR device 14 to calculate real-time carbon emissions based on load information and DR events.

Figure 2:
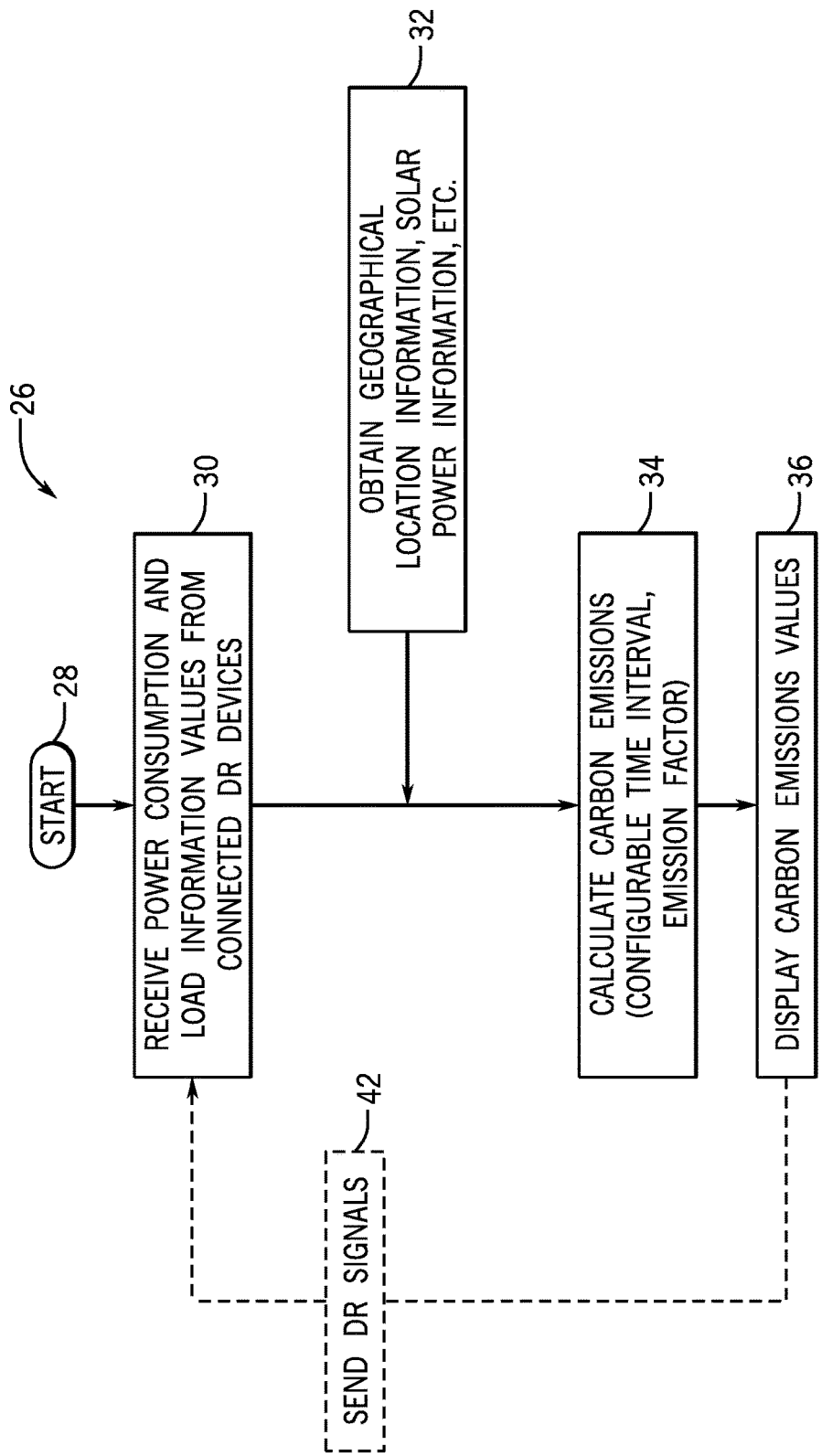
FIG. 2 is a flowchart illustrating a technique for calculating carbon emissions of the DR system of FIG. 1 at the electrical distribution substation, according to an embodiment of the invention.

In a first implementation, the carbon emissions calculator 24 is provided at the substation 12 (i.e., embedded in substation software of the computer 16 thereof) to calculate the substation's real-time carbon emissions based on the load information provided from connected DR devices 14. FIG. 2 illustrates a technique 26 for calculating the real-time carbon emissions at the substation 12. The technique begins at STEP 28 with the DR devices being operated according to customer commands/settings power and consuming power in association with such operation. At STEP 30, data on the power consumption and load information values associated with operation of the DR devices 14 that are part of the DR program is transmitted to the substation 12 and received thereby (i.e., at the computer/controller 16). In association with this power consumption and load information value data, additional information is provided to the substation 12 at STEP 32 regarding geographical location information on each of the DR devices 14 and power source data for/at each of the DR devices 14. For example, the power source data may include solar power information regarding an amount or presence of solar power generated at the DR device location (assuming this data would be available to the utility).

Upon obtaining power consumption and load information value data and related geographical location information and power source data at the substation 12, the technique continues to STEP 34, where carbon emissions are calculated for the connected DR devices 14. According to an exemplary embodiment, the carbon emissions are calculated in real-time via the following formula:

$$CO_2 \text{ emissions} = \text{Total electricity consumption (kWh value includes solar power)} \times \text{emissions factor (kg } CO_2/\text{kWh)} \quad [\text{Eqn. 1}],$$

where the total electricity consumption is calculated between a time period set by the utility (e.g., every minute, every hour, etc.) and the emissions factor is a known value that may be regularly updated by the utility on the basis of changes in energy source, weather information, etc.

Figure 3:
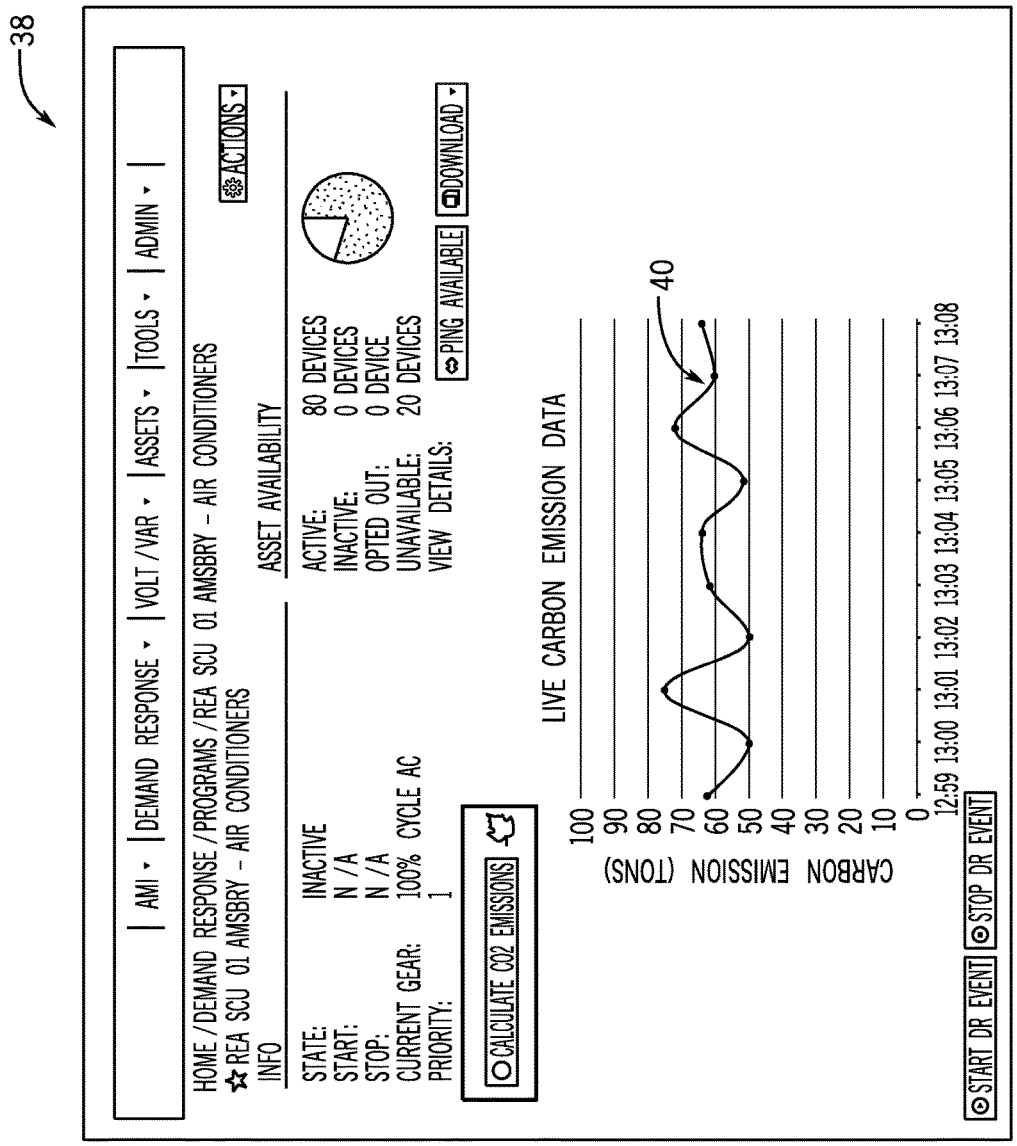
FIG. 3 is a screenshot of an exemplary graphical user interface (GUI) displaying calculated carbon emissions of the DR system, according to an embodiment of the invention.

In a next step of the technique 26, the calculated carbon emissions may then be displayed to a user or operator at STEP 36, with such display being provided via a graphical user interface (GUI) provided on a monitor or display of the computer 16 at substation 12 or another suitable display device. An example of a display 38 that might be generated illustrating such carbon emissions calculations is provided in FIG. 3. As shown therein, an emissions curve 40 is generated that provides carbon emissions data at pre-defined intervals, such as every minute in the illustrated curve. The display 38 could also include information on the number of active devices 14 providing data to the substation 12, as well as any inactive devices, opted out devices, and unavailable devices.

Figure 4:
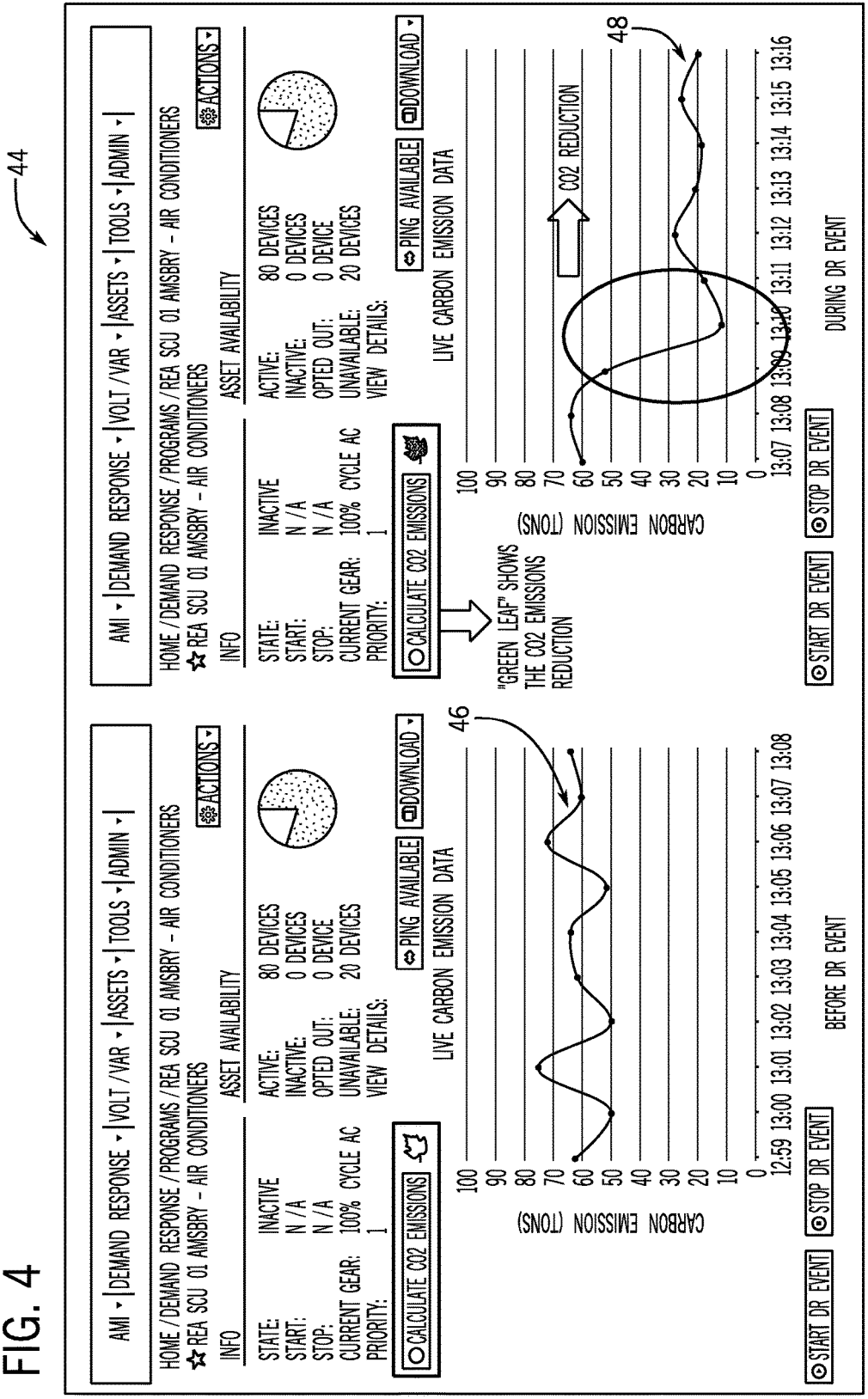
FIG. 4 is a screenshot of an exemplary graphical user interface (GUI) displaying calculated carbon emissions of the DR system, according to another embodiment of the invention.

It is recognized that calculation of the carbon emissions at the substation 12 for DR devices 14 connected thereto can provide not only data on the real-time carbon emissions for the devices, but can also provide for comparisons to be made between carbon emissions resulting from operation of the DR devices 14 prior to and during implementation of a DR event for one or more of the devices. That is, carbon emissions could be calculated at the substation 12 for the DR devices 14 connected thereto in a first iteration of technique 26 that is performed prior to implementation of a DR event and carbon emissions could then be again calculated at the substation 12 for the DR devices 14 connected thereto in a second iteration of technique 26 that is performed during implementation of a DR event (responsive to sending/transmission of a DR signal 22 to the devices, as performed at STEP 42 in FIG. 2), so as to enable a determination of a carbon emissions reduction achieved via implementation of the DR event. An example of a display 44 that might be generated illustrating such carbon emissions calculations prior to and during a commanded DR event is provided in FIG. 4. As shown therein, a first emissions curve 46 is generated that provides a carbon emissions reading at pre-defined intervals prior to implementation of a DR event, while a second emissions curve 48 is generated that provides a carbon emissions reading at pre-defined intervals during implementation of a DR event.

In another embodiment, the carbon emissions calculator 24 and operation thereof according to technique 26 provide not just for real-time carbon emissions data to be obtained, but also for calculation of carbon emissions for a past DR event and/or a forecast of carbon emissions for a future DR event. In an embodiment where carbon emissions is calculated for a past DR event, total electricity consumption and emissions factor data can be acquired for past operation of DR devices based on data received at STEPS 30 and 32, with such data being stored in a memory device of computer 16 (or a separate memory device) and accessible for later calculation of carbon emissions of past DR events. In an embodiment where carbon emissions is forecast for a future DR event, statistical analysis can be performed on previous carbon emissions calculations and their associated DR events to determine an estimate of what the carbon emissions will be for the future DR event. The calculation and forecast of carbon emissions for such past and future DR events may be commanded via a carbon emissions calculator button embedded into the substation software (i.e., on the GUI displays 38, 44 of FIGS. 3 and 4, for example).

In a second implementation, the carbon emissions calculator 24 is provided in each of the DR devices 14 (e.g., embedded in software of the controller 18 thereof) to calculate the device's real-time carbon emissions. Non-limiting examples of devices that might incorporate the carbon emissions calculator 24 therein include load control switches, power meters (LCR meters), thermostats, or the like, and their associated loads. The devices 14 may communicate their calculated carbon emissions to the substation 12 when communicating with the electrical software of the substation 12 as part of the general DR program and DR signals or communications protocol 22 (e.g., via wireless communication as part of the Yukon® program).

Figure 5:
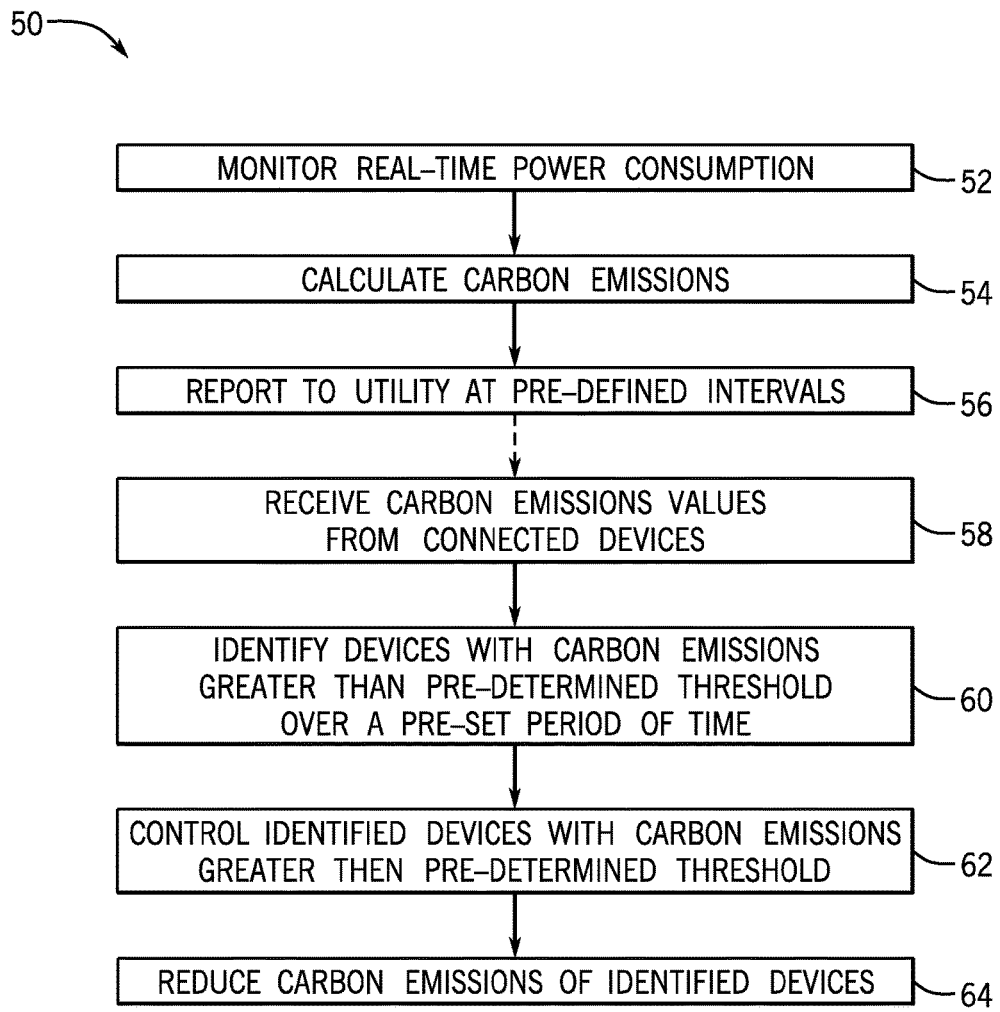
FIG. 5 is a flowchart illustrating a technique for calculating carbon emissions of a device in the DR system of FIG. 1 at a device level, according to an embodiment of the invention.

FIG. 5 illustrates a technique 50 for calculating the real-time carbon emissions at the device level—which allows a utility and customer to identify the carbon emissions of a specific device and/or, potentially, the carbon emissions of a collection of devices at a particular facility (i.e., residence or industrial facility). The technique 50 begins at STEP 52 with the DR device 14 being operated and the real-time power consumption of the device being monitored. Upon obtaining power consumption data, the technique continues to STEP 54, where carbon emissions are calculated for the DR device 14. As set forth previously, one example of the carbon emissions calculation performed in real-time is set forth in the formula:

$$CO_2 \text{ emissions} = \text{Total electricity consumption (kWh value includes solar power)} \times \text{emissions factor (kg } CO_2/\text{kWh)} \quad \text{[Eqn. 1]},$$

where the total electricity consumption is calculated between a time period set by the utility (e.g., every minute, every hour, etc.) and the emissions factor is a known value that may be regularly updated by the utility on the basis of changes in energy source, weather information, etc. power source data for/at each of the DR devices 14. Thus, regarding the emissions factor, information such as solar power information regarding an amount or presence of solar power generated at the DR device location may be accounted for, as such data is often available to a local facility/industry.

In a next step of the technique 50, the calculated carbon emissions may then be reported to the substation 12 at STEP 56, with such reporting being performed at pre-determined time intervals as deemed appropriate (e.g., every minute, every hour, etc.). The utility is therefore able to identify the carbon emissions being generated by a specific DR device 14 connected thereto.

In an exemplary embodiment, in addition to calculating the carbon emissions for a specified DR device 14, other beneficial actions can be taken by the utility responsive to the received carbon emissions data, with such an example being given in the technique 50—such as the technique further providing for control of the DR device 14 (and all other DR devices 14 from which carbon emissions data has been received) by the utility in order to reduce the carbon emissions of the devices. Thus, in next steps of technique 50, the substation receives the carbon emissions values from the DR device 14 at STEP 58 and monitors the values to identify DR devices 14 with carbon emissions that exceed a pre-determined threshold level (i.e., the devices reporting carbon values greater than a maximum allowed value) for a preset period of time, as indicated at STEP 60. As an example, the substation 12 may monitor the carbon emissions of a DR device 14 over a period of two weeks and then make a determination as to whether the carbon emissions of the DR device 14 exceed a pre-determined threshold level over that two week period.

In the event that the carbon emissions of any DR devices 14 connected to the substation 12 are determined to exceed the pre-determined carbon emissions threshold level over the preset period of time, the technique then continues to STEP 62, where any such identified DR devices 14 may be controlled by the substation 12 as part of the DR program in order to reduce the carbon emissions thereof. That is, at STEP 62, the utility may take necessary action on the identified devices, if agreed upon by the user, such as sending DR events or switching to solar installations, such that carbon emissions may be reduced. As one example, a DR event may be commanded/implemented for a two-way LCR meter in order to reduce power consumption on the load side and/or power the load by way of energy provided from a solar installation, so as to thereby reduce the carbon emissions of the device. Thus, upon implementing a DR event for the DR device 14 at STEP 62, the carbon emissions of the device is thus reduced—as indicated at STEP 64.

Beneficially, embodiments of the invention thus enable automatically determining the carbon emissions at the substation level and at the device level for each device connected to the substation using a demand response system and program. The calculated values can be aggregated at the utility level to geographically visualize the high-emission areas and green geographical areas and assist utilities in providing green certificates to devices. With solar power data at distribution level also being considered, an accurate method of assessing carbon emissions in a particular industry or locality can be provided.

Therefore, according to an embodiment of the invention, a system to calculate the carbon emissions of one or more devices operably connected to a utility substation to receive power therefrom is provided. The system includes a substation controller provided at the utility substation and in operable communication with the one or more devices via a demand response protocol, the demand response protocol including demand response signals transferrable from the substation controller to the one or more devices and demand response signals transferrable from the one or more devices to the substation controller. The system also includes a carbon emissions calculator module embedded in or operably connected to the substation controller, the carbon emissions calculator programmed to receive at least one of power consumption data and load information values from each of the one more devices via the demand response protocol, calculate carbon emissions for each of the one more devices based on the at least one of power consumption data and load information values, and generate an output indicating the calculated carbon emissions for each of the one more devices.

According to another embodiment of the invention, a system to calculate the carbon emissions of a power consuming device operably connected to a utility substation to receive power therefrom is provided. The system includes a power consuming or power monitoring device and a device controller configured to provide load control and power consumption modification for the device, the device controller in operable communication with the utility substation via a demand response protocol that comprises demand response signals transferrable from the utility substation to the device controller and demand response signals transferrable from device controller to the utility substation. The system also includes a carbon emissions calculator module embedded in or operably connected to the device controller, the carbon emissions calculator programmed to monitor a real-time power consumption of the device, calculate carbon emissions for the device based on the monitored power consumption, and generate an output signal comprising the calculated carbon emissions for the device, the output signal being transmittable to the utility substation via the demand response protocol.

According to yet another embodiment of the invention, a method for calculating the carbon emissions of one or more devices operably connected to a utility substation includes a step of providing a demand response system configured to implement a demand response protocol for interactions between a substation controller and the one or more devices, the demand response protocol including demand response signals transferrable from the substation controller to the one or more devices and demand response signals transferrable from the one or more devices to the substation controller to provide load control and power consumption modification for the one or more devices. The method also includes the steps of determining a power consumption of each of the one more devices resulting from an operation thereof and calculating, via a carbon emissions calculator module embedded in one of the substation controller or a respective device of the one or more devices, carbon emissions for each of the one more devices based on the power consumption.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system to calculate the carbon emissions of one or more devices operably connected to a utility substation to receive power therefrom, the system comprising:
   a substation controller provided at the utility substation and in operable communication with the one or more devices via a demand response protocol, the demand response protocol including demand response signals transferrable from the substation controller to the one or more devices and demand response signals transferrable from the one or more devices to the substation controller; and
   a carbon emissions calculator module embedded in or operably connected to the substation controller, the carbon emissions calculator programmed to:
      receive at least one of power consumption data and load information values from each of the one more devices via the demand response protocol;
      calculate carbon emissions for each of the one more devices based on the at least one of power consumption data and load information values;
      generate an output indicating the calculated carbon emissions for each of the one more devices;
   wherein the substation controller is programmed to selectively initiate a demand response event to control operation of the one or more devices based on the output, so as to:
      reduce a power consumption of the one or more devices, so as to also reduce the carbon emissions of the one or more devices; or
      alter a power source from which the one or more devices receive power, the altered power source comprising a renewable energy power source.

2. The system of claim 1 wherein the carbon emissions calculator is programmed to:
   calculate carbon emissions for each of the one more devices prior to initiation of a demand response event;
   calculate carbon emissions for each of the one more devices during or subsequent to initiation of a demand response event; and
   calculate an emissions reduction achieved for the one or more devices based on a subtraction of the calculated carbon emissions for each of the one more devices during or subsequent to initiation of the demand response event from the calculated carbon emissions for each of the one more devices prior to initiation of the demand response event.

3. The system of claim 2 wherein the carbon emissions calculator is programmed to calculate the emissions reduction in real-time.

4. The system of claim 2 wherein the carbon emissions calculator is programmed to calculate the emissions reduction for a previous demand response event, with the carbon emissions calculator programmed to:
   store the calculated carbon emissions for each of the one more devices for a period prior to initiation of a demand response event;
   store the calculated carbon emissions for each of the one more devices for a period subsequent to completion of a demand response event; and
   calculate the emissions reduction for the previous demand response event based on the stored carbon emissions.

5. The system of claim 2 wherein the carbon emissions calculator is programmed to forecast carbon emissions for a future demand response event via a statistical analysis performed on prior carbon emissions calculations and their associated demand response events.

6. The system of claim 1 wherein the carbon emissions calculator is programmed to receive geographical location information and power source data from each of the one more devices via the demand response protocol.

7. The system of claim 6 wherein the carbon emissions calculator is programmed to calculate the carbon emissions for each of the one more devices according to:

$$CO_2 \text{Emissions} = \text{Total electricity consumption (kWh value includes solar power)} \times \text{Emissions Factor (kg } CO_2/\text{kWh)},$$

where the total electricity consumption is calculated for a set time period and the emissions factor is a known value.

8. The system of claim 7 wherein the carbon emissions calculator is programmed to update the emissions factor based on the power source data received from each of the one more devices.

9. The system of claim 1 wherein, in generating the output indicating the calculated carbon emissions, the carbon emissions calculator is programmed to generate a display of the calculated carbon emissions on a graphical user interface of the substation controller, the display comprising at least one of a graphical display and a numerical display of the calculated carbon emissions.

10. A system to calculate the carbon emissions of a power consuming device operably connected to a utility substation to receive power therefrom, the system comprising:
a device comprising a power consuming or power monitoring device;
a device controller configured to provide load control and power consumption modification for the device, the device controller in operable communication with the utility substation via a demand response protocol that comprises demand response signals transferrable from the utility substation to the device controller and demand response signals transferrable from device controller to the utility substation;
a carbon emissions calculator module embedded in or operably connected to the device controller, the carbon emissions calculator programmed to:
monitor a real-time power consumption of the device;
calculate carbon emissions for the device based on the monitored power consumption; and
generate an output signal comprising the calculated carbon emissions for the device, the output signal being transmittable to the utility substation via the demand response protocol; and
a substation controller provided at the utility substation and in operable communication with the device via the demand response protocol, the substation controller programmed to:
receive a plurality of output signals generated by the carbon emissions calculator module indicating the calculated carbon emissions for the device over a pre-set period of time;
compare the calculated carbon emissions for the device to a carbon emissions threshold over the pre-set period of time; and
when the calculated carbon emissions for the device exceed the carbon emissions threshold over the pre-set period of time, initiate an action to reduce the carbon emissions of the device.

11. The system of claim 10 wherein, in initiating an action to reduce the carbon emissions of the device, the substation controller is programmed to initiate a demand response event to reduce a power consumption of the device, so as to also reduce the carbon emissions of the device.

12. The system of claim 10 wherein, in initiating an action to reduce the carbon emissions of the device, the substation controller is programmed to alter a power source from which the device receives power, the altered power source comprising a renewable energy power source.

13. The system of claim 10 wherein the carbon emissions calculator is programmed to calculate the carbon emissions for the device according to:

$$CO_2 \text{ Emissions} = \text{Total electricity consumption (kWh value includes solar power)} \times \text{Emissions Factor (kg } CO_2/\text{kWh)},$$

where the total electricity consumption is calculated for a set time period and the emissions factor is a known value.

14. The system of claim 10 wherein the device comprises one of a load control switch, a power meter, and a thermostat.

15. A method for calculating the carbon emissions of one or more devices operably connected to a utility substation, the method comprising:
providing a demand response system configured to implement a demand response protocol for interactions between a substation controller and the one or more devices, the demand response protocol including demand response signals transferrable from the substation controller to the one or more devices and demand response signals transferrable from the one or more devices to the substation controller to provide load control and power consumption modification for the one or more devices; and
determining a power consumption of each of the one more devices resulting from an operation thereof; and
calculating, via a carbon emissions calculator module embedded in one of the substation controller or a respective device of the one or more devices, carbon emissions for each of the one more devices based on the power consumption;
wherein, when the carbon emissions calculator module is embedded in a respective device of the one or more devices, the method further comprises:
generating an output signal from the device comprising the calculated carbon emissions for the device, the output signal being transmittable to the substation controller via the demand response protocol;
receiving at the substation controller a plurality of output signals generated by the carbon emissions calculator module indicating the calculated carbon emissions for the device over a pre-set period of time;
comparing at the substation controller the calculated carbon emissions for the device to a carbon emissions threshold over the pre-set period of time; and
when the calculated carbon emissions for the device exceed the carbon emissions threshold over the pre-set period of time, initiating at the substation controller an action to reduce the carbon emissions of the device.

16. The method of claim 15 wherein, when the carbon emissions calculator module is embedded in the substation controller, the method further comprises:
calculate carbon emissions for each of the one more devices prior to initiation of a demand response event, the demand response event being implemented by the substation controller to control operation of the one or more devices so as to provide power consumption modification for the one or more devices;

calculate carbon emissions for each of the one more devices during or subsequent to initiation of a demand response event; and calculate an emissions reduction achieved for the one or more devices based on a subtraction of the calculated carbon emissions for each of the one more devices during or subsequent to initiation of the demand response event from the calculated carbon emissions for each of the one more devices prior to initiation of the demand response event.

17. The method of claim 15 wherein, when the carbon emissions calculator module is embedded in the substation controller, the method further comprises receiving geographical location information and power source data from each of the one more devices via the demand response protocol, the power source data indicating a presence of any power provided to a respective device from a renewable solar energy source.

\* \* \* \* \*

UNITED STATES PATENT AND TRADEMARK OFFICE
CERTIFICATE OF CORRECTION

PATENT NO. : 10,444,210 B2  
APPLICATION NO. : 15/223256  
DATED : October 15, 2019  
INVENTOR(S) : Rawat et al.

Page 1 of 1

It is certified that error appears in the above-identified patent and that said Letters Patent is hereby corrected as shown below:

On the Title Page

(73) Assignee: delete "Baton" and substitute therefore -- Eaton --.

Signed and Sealed this  
Seventh Day of January, 2020

Andrei Iancu  
*Director of the United States Patent and Trademark Office*